US009944594B2

(12) United States Patent
Fremy et al.

(10) Patent No.: US 9,944,594 B2
(45) Date of Patent: Apr. 17, 2018

(54) CATALYST FOR THE SYNTHESIS OF METHYL MERCAPTAN AND PROCESS FOR PRODUCING METHYL MERCAPTAN FROM SYNTHESIS GAS AND HYDROGEN SULPHIDE

(71) Applicant: Arkema France, Colombes (FR)

(72) Inventors: Georges Fremy, Sauveterre de Bearn (FR); Patrice Barre, Lons (FR); Karine Sanchou, Pau (FR); Alexia Cordova, Lille (FR); Carole Lamonier, Armentieres (FR); Pascal Blanchard, Lens (FR)

(73) Assignee: ARKEMA FRANCE, Colombes (FR)

( * ) Notice: Subject to any disclaimer, the term of this patent is extended or adjusted under 35 U.S.C. 154(b) by 0 days.

(21) Appl. No.: 14/781,171

(22) PCT Filed: Mar. 28, 2014

(86) PCT No.: PCT/EP2014/056343
§ 371 (c)(1),
(2) Date: Sep. 29, 2015

(87) PCT Pub. No.: WO2014/154885
PCT Pub. Date: Oct. 2, 2014

(65) Prior Publication Data
US 2016/0326105 A1 Nov. 10, 2016

(30) Foreign Application Priority Data
Mar. 29, 2013 (FR) ...................... 13 52871

(51) Int. Cl.
C07C 319/02 (2006.01)
B01J 23/28 (2006.01)
B01J 27/18 (2006.01)
B01J 35/00 (2006.01)
C07C 319/06 (2006.01)
B01J 27/057 (2006.01)
B01J 23/755 (2006.01)
B01J 23/745 (2006.01)
B01J 37/02 (2006.01)
B01J 27/051 (2006.01)
B01J 35/10 (2006.01)

(52) U.S. Cl.
CPC ............ *C07C 319/02* (2013.01); *B01J 23/28* (2013.01); *B01J 23/745* (2013.01); *B01J 23/755* (2013.01); *B01J 27/051* (2013.01); *B01J 27/0576* (2013.01); *B01J 27/1806* (2013.01); *B01J 35/0006* (2013.01); *B01J 35/1014* (2013.01); *B01J 37/0201* (2013.01); *B01J 37/0207* (2013.01); *C07C 319/06* (2013.01)

(58) Field of Classification Search
None
See application file for complete search history.

(56) References Cited

U.S. PATENT DOCUMENTS

2007/0213564 A1    9/2007   Yang
2010/0021734 A1*   1/2010   Uemoto ................. B01J 20/048
                                                              428/402
2010/0094059 A1    4/2010   Yang
2010/0286448 A1   11/2010   Yang

FOREIGN PATENT DOCUMENTS

CN    1207958 A   *  2/1999    ............... B01J 23/28
EP    0149255 A2  *  7/1985    ............... C07C 29/15
EP    0571090         11/1993
WO    2005040082       5/2005

OTHER PUBLICATIONS

Gutirrez, O Y et al., "Synthesis of methyl mercaptan from carbonyl sulfide over sulfide K2MoO4/SiO2" Journal of Catalysis, vol. 280, No. 2, Mar. 26, 2011, pp. 264-273.
International Search Report for International Application No. PCT/EP2014/056343 dated May 9, 2014.
Lamonier, C. et al., "Specific tuning of acid/base sites in apatite materials to enhance their methanol thiolation catalytic performances," Catalysis Today, vol. 164, No. 1, Nov. 4, 2010, pp. 124-130.
Written Opinion of the International Searching Authority for International Application No. PCT/EP2014/056343 dated May 9, 2014.
Yang, Y-Q et al., "Study of the supported K2MoO4 catalyst for methanethiol synthesis by one step from high H2S-containing syngas," Catalysis Letters, vol. 74, No. 3-4, Jan. 1, 2001, pp. 221-225.
Yang, Y-Q et al., "The catalytic properties of supported K2MoS4/SiO2 catalyst for methanethiol synthesis from high H2S-content syngas," Catalysis Letters, vol. 54, No. 1/02, Sep. 1, 1998, pp. 65-68.

* cited by examiner

*Primary Examiner* — Rosalynd A Keys
(74) *Attorney, Agent, or Firm* — RatnerPrestia

(57) ABSTRACT

The invention relates to a catalyst comprising an active component based on molybdenum and on potassium and a support based on hydroxyapatite, and also to a process for preparing said catalyst and a process for producing methyl mercaptan in a catalytic process by reaction of carbon monoxide, sulphur and/or hydrogen sulphide and hydrogen, comprising the use of said catalyst.

20 Claims, No Drawings

CATALYST FOR THE SYNTHESIS OF METHYL MERCAPTAN AND PROCESS FOR PRODUCING METHYL MERCAPTAN FROM SYNTHESIS GAS AND HYDROGEN SULPHIDE

CROSS-REFERENCE TO RELATED APPLICATIONS

This is a national phase application of International Application No. PCT/EP2014/056343, filed Mar. 28, 2014, which claims priority from French Application No. 1352871, filed Mar. 29, 2013, the disclosures of each of which are incorporated herein by reference in their entireties for all purposes.

The work that led to this invention received financing from the European Union as part of the 7th Framework Programme (FP7/2007-2013) under project number No. 241718 EUROBIOREF.

The present invention relates to a specific molybdenum- and potassium-based catalyst that is useful for producing methyl mercaptan from synthesis gas and hydrogen sulfide, and to its preparation process.

The invention also relates to a process for producing methyl mercaptan that uses this catalyst.

The invention lastly relates to the use of hydroxyapatite as a support for a catalyst for producing methyl mercaptan.

Methyl mercaptan has great industrial interest, particularly as a raw material for synthesizing methionine, an essential amino acid that is in widespread use in animal food. Methyl mercaptan is also a raw material for many other molecules, in particular dimethyldisulfide (DMDS), a sulfidation additive for hydrotreating catalysts in petroleum fractions, among other applications.

Methyl mercaptan is commonly produced in large tonnages industrially from methanol and hydrogen sulfide. It may prove economically interesting to want to produce methyl mercaptan directly from carbon monoxide, hydrogen and hydrogen sulfide according to the following reaction scheme:

$$CO + 2H_2 + H_2S \rightarrow CH_3SH + H_2O \quad (1)$$

The main by-product from this synthesis is carbon dioxide. Carbonyl sulfide (COS) is considered to be the reaction intermediate, which leads to methyl mercaptan after hydrogenation according to the following reaction schemes:

$$CO + H_2S \rightarrow COS + H_2 \quad (2)$$

$$COS + 3H_2 \rightarrow CH_3SH + H_2O \quad (3)$$

The carbon dioxide comes from two side reactions:

$$CO + H_2O = CO_2 + H_2 \quad (4)$$

and $$COS + H_2O \rightarrow CO_2H_2S \quad (5)$$

These two side reactions, which consume the main raw material: carbon monoxide, and the reaction intermediate: carbonyl sulfide, are due to the inescapable presence of water, coproduced during methyl mercaptan synthesis. The carbon dioxide can optionally be recycled to produce methyl mercaptan as well according to the following scheme:

$$CO_2 + 3H_2 + H_2S \rightarrow CH_3SH + 2H_2O \quad (6)$$

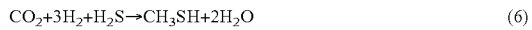

But this reaction is known to be slower than that from carbon monoxide. Therefore there is incentive to make carbon dioxide production as low as possible at the outlet of the methyl mercaptan reactor.

From document WO2005/040082 several catalysts are known for the synthesis of methyl mercaptan from synthesis gas and hydrogen sulfide.

In particular, this document discloses the use of a catalyst comprising a Mo—O—K based active component, an active promoter and optionally a support. The catalysts exemplified have different chemical natures, such as $K_2MoO_4/Fe_2O_3NiO$ or $K_2MoO_4/CoO/CeO_2/SiO_2$, each supported on silica. This leads to a $CO_2$/MeSH selectivity ratio of 0.88 at 333° C.

A family of catalysts composed of a porous support onto which a metal has been deposited electrolytically is also known from document US2010/0286448. $K_2MoO_4$ and another metal oxide as promoter were then impregnated onto this support. Example 15 of this document describes the preparation of $K_2MoO_4/NiO/CoSiO_2$. The $CO_2$/MeSH selectivity ratio with this complex catalyst is 0.65.

Lastly, US document 2010/0094059 describes supported $K_2MoO_4$ based catalysts, where the porous support used alone or in mixtures is chosen from $SiO_2$, $Al_2O_3$, $TiO_2$, $Al_2O_3/SiO_2$, $ZrO_2$, zeolites or carbon-containing materials. Tellurium oxide ($TeO_2$) is used as promoter. The $CO_2$/MeSH selectivity ratios are comprised between 0.60 and 0.77 measured at 300° C.

From the teaching of these documents it has been observed that combining catalysts with specific structures, promoters and supports, each being carefully selected, means that interesting selectivity ratios can be achieved.

There is a current need for a catalyst that is simply synthesized and leads to very good selectivity. This technical problem has been resolved by a molybdenum- and potassium-based catalyst supported by hydroxyapatite.

It has been observed that the catalyst according to the invention is easier to prepare, given that the presence of a promoter is not indispensable. It is less costly than those disclosed in the previously cited documents. And lastly, it leads to very good $CO_2$/MeSH selectivities.

The invention also relates to the preparation process for this catalyst.

The invention also relates to a process for producing methyl mercaptan from synthesis gas and hydrogen sulfide using the catalyst according to the invention.

The invention also relates to the use of the catalyst as defined above for the synthesis of methyl mercaptan from synthesis gas and hydrogen sulfide.

Lastly the invention relates to the use of hydroxyapatite as support for preparing a catalyst for producing methyl mercaptan, and in particular in a catalytic process by reacting carbon oxide, sulfur and/or hydrogen sulfide and hydrogen.

Other characteristics, features, subjects and benefits of the present invention will emerge even more clearly on reading the description and the examples that follow.

Any range of values denoted by the expression "between a and b" represents the values ranging from more than a to less than b (i.e. limits a and b excluded), while any range of values denoted by the expression "from a to b" means the values ranging from a to b (i.e. including the limits a and b).

Catalyst

The present invention relates to a catalyst.

This catalyst comprises a molybdenum- and potassium-based active component and a hydroxyapatite-based support.

Active Component

The active component present in the catalyst according to the invention comprises molybdenum and potassium within a single component.

Preferably, the molybdenum- and potassium-based active component is chosen from compounds based on Mo—S—K, compounds based on Mo—O—K, and their mixtures.

The Mo—S—K based active component may be obtained by deposit and calcination of $K_2MoS_4$ or $(NH_4)_2 MoS_4$ precursors with impregnated $K_2CO_3$ added separately to the support.

The Mo—O—K based active component may be obtained by deposit and calcination of $K_2MoO_4$ or $(NH_4)_2 MoO_4$ precursors with impregnated $K_2CO_3$ added separately to the support.

It is also possible to use ammonium heptamolybdate $(NH_4)_6Mo_7O_{24}.4H_2O$ as reagent, in the presence of a potassium salt such as for instance potassium nitrate $KNO_3$, potassium carbonate $K_2CO_3$ or potassium hydroxide $KOH$.

These compounds are precursors of Mo—S—K and Mo—O—K based active phases respectively. The active phases are obtained after in situ precursor pretreatment, with for example a procedure consisting in a first step of drying in nitrogen at 250° C., followed by sulfidation with hydrogen sulfide at the same temperature for 1 hour, then a step of reduction/sulfidation with $H_2/H_2S$ at 350° C. for 1 hour.

Support

The catalyst support according to the invention is hydroxyapatite having formula $Ca_{10}(PO_4)_6(OH)_2$, advantageously a stoichiometric hydroxyapatite.

Preferably, hydroxyapatite that is useful according to the present invention has a Ca/P molar ratio ranging from 1.5 to 2.1, and more preferably 1.67, corresponding to the expected value for stoichiometric hydroxyapatite.

Preferably, the weight ratio of the catalyst according to the invention is:

$$K_2MoS_4/Ca_{10}(PO_4)_6(OH)_2=31.3/100$$

$$K_2MoO_4/Ca_{10}(PO_4)_6(OH)_2=50.7/100$$

The catalytic activity may be improved by using a support material having a specific area greater than 25 $m^2/g$.

Preferably, the hydroxyapatite supports according to the invention have a specific area of at least 40 $m^2/g$, more specifically the specific area ranges from 40 $m^2/g$ to 300 $m^2/g$ and a Ca/P molar ratio of 1.67.

The structure of the support may be three dimensional, spherical, cylindrical, ring-shaped, star-shaped, granulates or any other three dimensional shape, or in the form of a powder, which can be pressed, extruded, granulated or in a three dimensional shape.

Preferably, the catalyst particles have uniform particle size distribution with diameter from 0.1 mm to 20.0 mm measured by sieve analysis.

Promoter

Preferably, the catalyst according to the invention consists in a molybdenum- and potassium-based active component and a hydroxyapatite-based support.

However, it is possible to envisage the presence of a promoter known to the person skilled in the art, such as tellurium oxide, nickel oxide or iron oxide.

Catalyst Preparation Process

The invention also relates to the preparation process for the catalyst according to the invention. This process comprises the following successive steps:
preparing the precursor for the active phase
preparing the support, and
dry impregnating the support with the active phase precursor.

Preparing the Precursor for the Active Phase

1/Mo—O—K

1. The $K_2MoO_4$ salt is a commercial salt. To prepare the Mo—O—K based-catalyst, a fixed quantity of $K_2MoO_4$ is dissolved in a volume of water to obtain a solution with desired concentration, such as for example a concentration ranging from 0.5-1.0 g/mL.

2. It is also possible to begin with separated molybdenum and potassium salts, i.e. that are not part of the same compound. For this synthesis, a molybdenum-based solution is prepared by adding ammonium heptamolybdate in water to obtain a $MoO_3$ concentration ranging from 22 to 33% by weight.

In parallel, a potassium-based solution is prepared by adding potassium nitrate in water to obtain a $K_2O$ concentration ranging from 31 to 43% by weight.

2/Mo—S—K

The $K_2MoS_4$ synthesis is generally done in two steps.

The first step involves preparing ammonium tetrathiomolybdate (ATTM); the second step is the synthesis of potassium tetrathiomolybdate ($K_2MoS_4$) from the salt prepared in the first step.

To prepare ATTM, hydrogen sulfide is left to bubble continuously in a 25% aqueous ammonia solution, in which ammonium heptamolybdate (HMA) has been dissolved. The solution temperature increases, indicating an exothermic reaction. The hydrogen sulfide bubbling is stopped when the temperature falls (generally after one hour).

The solution then contains red crystals with green reflections, which correspond to ammonium tetrathiomolybdate.

The second step consists in an ion exchange between ammonium ions in the ammonium tetrathiomolybdate salt obtained and potassium ions, which come from a potassium hydroxide solution. The salts obtained are then stored under vacuum. A quantity of potassium tetrathiomolybdate is dissolved in water.

The potassium salt useful in the catalyst according to the present invention may come from the following compounds: potassium acetate (KAc), potassium oxalate ($K_2C_2O_4$), potassium hydroxide (KOH), potassium carbonate ($K_2CO_3$), potassium nitrate ($KNO_3$), and potassium bicarbonate ($KHCO_3$).

Support Preparation

The catalyst support, constituted of hydroxyapatite, is prepared by a coprecipitation method. An aqueous solution of calcium nitrate $Ca(NO_3)_2$ was added dropwise to an ammonium hydrogenphosphate $(NH_4)H_2PO_4$ solution with stirring. The temperature is held at 100° C. and the pH is held at 10 with addition of an ammonia solution (25%).

The resulting white precipitate is filtered, washed, dried at 80° C. overnight and calcinated at 400° C. The hydroxyapatite $Ca_{10}(PO_4)_6(OH)_2$ was obtained with a Ca/P molar ratio of 1.67 corresponding to the expected value for a stoichiometric hydroxyapatite.

Dry Impregnating the Support with the Active Phase Precursor

1/Mo—O—K

The dry impregnation method is used to prepare the catalyst. The $K_2MoO_4$ solution is impregnated in one step on the support. When the solutions containing potassium and molybdenum are distinct, the impregnation is done in 2 steps.

2/Mo—S—K

A potassium tetrathiomolybdate solution is then impregnated onto hydroxyapatite. The molybdate content in the catalyst depends on the $K_2MoS_4$ or $K_2MoO_4$ solubility and the support's porous volume.

The $K_2MoS_4$ solubility is between 0.25 g/mL and 0.50 g/mL (0.35 g/mL) and the $K_2MoO_4$ solubility is between 0.50 g/mL and 1.50 g/mL (0.90 g/mL). The support's porous volume is between 0.8 mL/g and 2.2 mL/g.

Consequently, the volume of solution used is calculated to obtain the desired weight ratio, and preferably the weight ratio as defined above.

After impregnation, the solid undergoes a maturation step for 2 hours, then oven drying at 80° C. for 24 hours, and calcination under gas flow (typically air) at 490° C. for 4 hours. If a second impregnation step is necessary, the solid undergoes the maturation, drying and calcination steps again.

Production Process for Methyl Mercaptan

The invention relates to a production process for methyl mercaptan in a catalytic process by reacting carbon oxide, sulfur and/or hydrogen sulfide and hydrogen, comprising the use of a catalyst as defined above.

The CO or $CO_2/H_2S/H_2$ molar ratios range from 1/1/0 to 1/8/8, or when sulfur is used to replace hydrogen sulfide, the molar ratios of CO or $CO_2/H_2S/H_2/S$ reagents range from 1/1/0/1 to 1/8/8/8.

Preferably, the CO or $CO_2/H_2S/H_2$ molar ratios range from 1/2/1 to 1/4/4; when sulfur is used to replace hydrogen sulfide, the molar ratios of CO or $CO_2/H_2S/H_2/S$ reagents range from 1/2/2/1 to 1/4/4/4.

These molar ratios take $CO_2$ into account. Therefore, they consider both reaction scheme (1) and reaction scheme (6).

Preferably, the reaction may occur in fixed tubular, multitubular, catalytic wall micro-channel or fluid bed reactors.

The invention also relates to the use of the catalyst as defined above for the production of methyl mercaptan from synthesis gas and hydrogen sulfide.

Lastly the invention relates to the use of hydroxyapatite as support for preparing a catalyst for producing methyl mercaptan, and in particular in a catalytic process by reacting carbon oxide, sulfur and/or hydrogen sulfide and hydrogen.

The present invention will now be described in the examples below, these examples being given only for illustration, and are of course not limiting.

EXAMPLES

Example 1

The catalyst according to the invention is prepared according to the dry impregnation method, as defined above. The resulting catalyst has the following characteristics:

TABLE 1

| Elemental analysis of the catalyst | | | | |
|---|---|---|---|---|
| Catalyst | Chemical composition | | | |
| (% by weight) | Mo | K | S | N |
| $K_2MoS_4$/Hap | 9.9 | 8.1 | 13.3 | <0.10 |

Example 2

The catalyst used is $K_2MoO_4$ on hydroxyapatite

Example 3

The catalyst tested is $K_2MoO_4$ on $SiO_2$

Example 4

The catalyst tested is $K_2MoS_4$ on $Al_2O_3$

Example 5

The catalyst tested is $K_2MoO_4$ on $Al_2O_3$.

Evaluating the Catalysts

The catalysts are evaluated in a reaction to produce methyl mercaptan in a fixed-bed reactor in the following conditions:
Temperature: 280° C.,
Pressure: 10 bars,
Composition of $CO/H_2/H_2S=1/2/1$ feed gas (v/v),
GHSV (Gas Hourly Space Velocity)=1333 $h^{-1}$ The reagents and products were analyzed in-line by gas chromatography.

Before the test, the catalysts were activated in situ with a first procedure consisting in a first step of drying in nitrogen at 250° C., followed by sulfidation with hydrogen sulfide at the same temperature for 1 hour, then a step of reduction/sulfidation with $H_2/H_2S$ at 350° C. for 1 hour.

The results are in table 2 below.

TABLE 2

| Results of catalytic tests | | | | | |
|---|---|---|---|---|---|
| | | Molar selectivities (%) | | | |
| Examples | Catalyst | $CH_3SH$ | COS | $CO_2$ | $CO_2/CH_3SH$ ratio |
| 1 (inv) | $K_2MoS_4$/Hap | 44.1 | 23.3 | 32.6 | 0.74 |
| 2 (inv) | $K_2MoO_4$/Hap | 43.3 | 23.6 | 31.9 | 0.74 |
| 3 (comp) | $K_2MoO_4/SiO_2$ | 48.8 | 5.3 | 45.3 | 0.93 |
| 4 (comp) | $K_2MoS_4/Al_2O_3$ | 45.0 | 7.3 | 46.6 | 1.04 |
| 5 (comp) | $K_2MoO_4/Al_2O_3$ | 47.0 | 3.4 | 49.6 | 1.06 |

The results presented in table 2 show that the catalysts according to the invention (examples 1 and 2) give much lower $CO_2$ (undesired product) selectivities than catalysts on the supports in the prior art (silica: example 3 or alumina: examples 4 and 5).

The selectivities are compared using carbon monoxide isoconversion, where this conversion is expressed by $m^2$ of specific air in the catalyst.

By comparing the results obtained with catalysts 1 and 4, we observe a 30% improvement in ratio, and this improvement is linked to choosing hydroxyapatite as support.

The same observation is seen when comparing example 2 according to the invention and examples 3 and 5.

We observe increased methyl mercaptan selectivity compared to the carbon dioxide produced according to a side reaction.

It should be noted that this selectivity is obtained without aid from the promoter such as tellurium oxide, nickel oxide or iron oxide as described in the prior art.

The invention claimed is:
1. A process for producing methyl mercaptan in a catalytic process by reacting carbon oxide, sulfur and/or hydrogen sulfide and hydrogen, comprising using a catalyst comprising a molybdenum- and potassium-based active component and a hydroxyapatite-based support.
2. The process of claim 1, wherein the hydroxyapatite of the hydroxyapatite-based support has a Ca/P molar ratio ranging from 1.5 to 2.1.

3. The process of claim 1, wherein the hydroxyapatite of the hydroxyapatite-based support has, a Ca/P molar ratio of 1.67.

4. The process of claim 1, wherein the hydroxyapatite-based support specific area greater than 25 m²/g.

5. The process of claim 1, wherein the hydroxyapatite-based support has a specific area greater than 40 m²/g.

6. The process of claim 1, wherein h catalyst support is hydroxyapatite having stoichiometric formula $Ca_{10}(PO_4)_6(OH)_2$.

7. The process of claim 6, wherein the molybdenum- and potassium-based active component is selected from the group consisting of compounds based on Mo—S—K, compounds based on Mo—O—K, and their mixtures.

8. The process of claim 7, wherein the molybdenum- and potassium- sed active component has been obtained from a precursor having structure $K_2MoS_4$.

9. The process of claim 8, wherein the weight ratio of $K_2MoS_4$ and $Ca_{10}(PO_4)_6(OH)_2$ used to obtain the catalyst is:

$K_2MoS_4/Ca_{10}(PO_4)_6(OH)_2=31.3/100.$

10. The process of claim 7, wherein the molybdenum and potassium-based active component has been obtained from a precursor having structure $K_2MoS_4$.

11. The process of claim 10, wherein the weight ratio of $K_2MoS_4$ and $Ca_{10}(PO_4)_6(OH)_2$ used to obtain the catalyst is:

$K_2MoO_4/Ca_{10}(PO_4)_6(OH)_2=50.7/100.$

12. The process of claim 1, wherein the hydroxyapatite is a stoichiometric hydroxyapatite.

13. The process of claim 1, wherein the catalyst does not include a promoter.

14. The process of claim 1, wherein the catalyst includes a promoter.

15. The process of claim 1, wherein the carbon oxide is CO or $CO_2$.

16. The process of claim 15, wherein the CO or $CO_2/H_2S/H_2$ molar ratios range from 1/1/0 to 1/8/8.

17. The process of claim 15, wherein the molar ratios of CO or $CO_2/H_2S/H_2/S$ reagents range from 1/1/0/1 to 1/8/8/8.

18. The process of claim 15, wherein the CO or $CO_2/H_2S/H_2$ molar ratios range from 1/2/1 to 1/4/4.

19. The process of claim 15, wherein the molar ratios of CO or $CO_2/H_2S/H_2/S$ reagents range from 1/2/2/1 to 1/4/4/4.

20. The process of claim 1, wherein the catalyst is prepared by a process comprising:
preparing a precursor for the molybdenum- and potassium-based active component;
preparing the hydroxyapatite-based support; and,
dry impregnating the hydroxyapatite-based support with the precursor for the molybdenum- and potassium-based active component.

* * * * *